Oct. 14, 1952 A. P. HOWARD Plant Pat. 1,136
ROSE PLANT
Filed Aug. 28, 1951
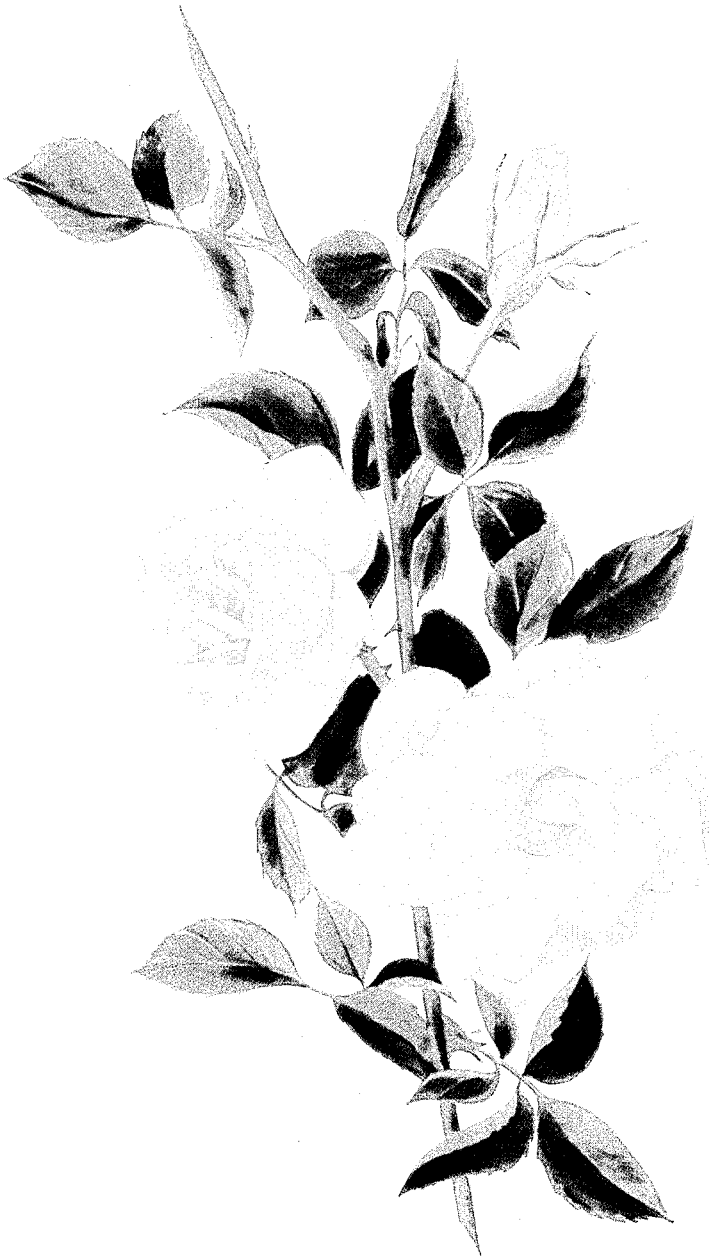
INVENTOR
Arthur Preston Howard
By Orville M. Kile
Plant Patent Agent Patented Oct. 14, 1952

Plant Pat. 1,136

UNITED STATES PATENT OFFICE 1,136

ROSE PLANT

Arthur Preston Howard, Sierra Madre, Calif., assignor to Howard & Smith, Montebello, Calif.

Application August 28, 1951, Serial No. 243,985

1 Claim. (Cl. 47—61)

My present discovery relates to a new and distinct variety of rose plant, originating as a sport of the variety California (Plant Patent No. 449). It is distinguished from its parent principally by its climbing habit including the position of the flowers, and the color of its flowers. The flowers are not a definite bi-color like those of the parent variety but the coloring is a modified and softened version of the flowers of the parent variety.

The parent plant is a bush rose of the hybrid tea class which has never, so far as I know, exhibited a climbing habit although it is a vigorous grower.

My new climbing rose variety was discovered by me at our nurseries in southern California, in the usual routine of nursery work. It has been asexually reproduced at the same location, by budding, and its characteristics appear to be permanent.

The accompanying illustrations show in approximately true colors, a portion of a branch of my new variety with several blooms in various stages of opening as they grow along the side of the stem, which is typical of climbing varieties.

In the following description, color plate numbers refer to Ridgway's Color Standards and Nomenclature and other color references indicate the usual dictionary meaning.

*The plant*

Class: Climbing hybrid tea.

Growth habit: Climbing; robust. Has attained a height of about 6 feet in one year.

Blooming habit: Profuse bloomer, producing good flowers continuously from March through October in southern California.

Stems: Strong. Tinged with Oxblood Red (Pl. I).

Thorns: Numerous; downward-pointing; red tinged; ¼ to ½ inch long.

Foliage:

*Type.*—Odd pinnate, with 3 to 5 leaflets.

*Shape.*—Elliptical, with acute apex.

*Size.*—Medium—terminal leaflet averaging 1½ to 2½ inches long by 1 to 1¼ inches wide.

*Texture.*—Leathery.

*Quantity.*—Normal.

*Color.*—Approximately Elm Green (Pl. XVII).

*Stipules.*—Prominent; clinging.

*Rachis.*—Short; smooth.

*Disease resistance.*—Very resistant to mildew and blackspot.

*The flower*

Bud:

*Size.*—Medium to large, averaging 1½ inch just before breaking and 2 to 2½ inches when beginning to spread.

*Shape.*—Long; pointed.

*Color.* — Approximately Salmon - Orange (Plate II) with touches of Rose Color Plate XII).

*Peduncle.*—Short, measuring 2 to 4 inches long.

*Sepals.*—Rather long (approximately 1½ inches); branched; hooded above tight bud. Calyx about ½ inch wide.

Bloom:

*Borne.*—Singly or in groups usually of three.

*Size.*—Medium, expanding to 3 inches.

*Form.*—Globular with high center, becoming loose and somewhat informal.

*Petalage.*—Semi-double, averaging about 20 to 25 petals.

*Color.*—The general color effect is Light Salmon Orange to Salmon Orange (Plate II), suffused with soft pink. The darker tones appear on the reverse side of the petals.

*Fragrance.*—Strong tea.

*Longevity.*—A very good keeper.

Petals:

*Shape.*—Cuneate-orbicular.

*Substance.*—Heavy.

*Size.*—1¾ inches from base to tip, on an average.

*Edge.*—Smooth.

*Behavior.*—Persistent.

*Color.*—The individual petal is darker on the reverse side than on the upper surface. In the spring much of the inner surface is Light Salmon Orange to Salmon Orange (Plate II) with a suffusion of soft pink at the edge. More pink is in evidence in the fall flowers and the entire coloring is intensified at that time.

Reproductive organs:

*Pistils.*—Prominent; many; bunched in center of flower and rise above stamens. Styles—red-tinged and rather long. Stigmas—light yellow.

*Stamens.*—Numerous; uneven; surround pistils. Anthers—large and bright yellow. Filaments—slender.

*Pollen.*—Average quantity. Light Orange-Yellow (Plate III).

Having thus disclosed my discovery, I claim:

The new and distinct variety of hybrid tea rose plant, in many respects similar to its parent but characterized particularly as to novelty by its robust, climbing habit of growth; the position of its blooms on the stems; and its bloom of medium size and approximately salmon-orange suffused with pink, substantially as shown and described.

ARTHUR PRESTON HOWARD.

No references cited.